United States Patent [19]
Eaves, III

[11] Patent Number: 6,143,008
[45] Date of Patent: *Nov. 7, 2000

[54] APPARATUS FOR ENDOSCOPIC HARVESTING OF ELONGATE TISSUE STRUCTURES

[76] Inventor: Felmont F. Eaves, III, 4927 Morrowick Rd., Charlotte, N.C. 28226

[*] Notice: This patent is subject to a terminal disclaimer.

[21] Appl. No.: 09/286,709

[22] Filed: Apr. 5, 1999

Related U.S. Application Data

[63] Continuation-in-part of application No. 08/991,976, Dec. 17, 1997.

[51] Int. Cl.⁷ .................................................. A61B 17/22
[52] U.S. Cl. ........................ 606/159; 606/160; 606/170
[58] Field of Search ..................................... 606/159, 160, 606/170, 171, 180; 600/210, 116

[56] References Cited

U.S. PATENT DOCUMENTS

| | | |
|---|---|---|
| 4,493,320 | 1/1985 | Treat . |
| 4,793,346 | 12/1988 | Mindich . |
| 4,821,718 | 4/1989 | Uldall . |
| 5,282,799 | 2/1994 | Rydell . |
| 5,318,564 | 6/1994 | Eggers . |
| 5,358,485 | 10/1994 | Vance et al. . |
| 5,373,840 | 12/1994 | Knighton . |
| 5,556,405 | 9/1996 | Lary . |
| 5,573,535 | 11/1996 | Viklund . |
| 5,591,183 | 1/1997 | Chin . |
| 5,601,581 | 2/1997 | Fogarty et al. . |
| 5,603,711 | 2/1997 | Parins et al. . |
| 5,634,935 | 6/1997 | Taheri . |
| 5,667,480 | 9/1997 | Knighy ................................. 600/210 |
| 5,695,514 | 12/1997 | Chin . |
| 6,019,771 | 2/2000 | Bennett et al. ...................... 606/159 |
| 6,022,313 | 2/2000 | Ginn et al. ........................... 600/114 |

FOREIGN PATENT DOCUMENTS

WO 97 21398  6/1997  WIPO .

*Primary Examiner*—Michael Buiz
*Assistant Examiner*—Lien Ngo
*Attorney, Agent, or Firm*—Alston & Bird LLP

[57] ABSTRACT

Apparatus and method for endoscopically harvesting an elongate structure such as a blood vessel or nerve from a patient's body. A harvesting head defines a channel for receiving a blood vessel or the like and an outer surface for dissecting and retracting connective tissue surrounding a vessel received in the channel. The head may have a substantially ovate shape and may depend from an extended handle. The head has at least one slot that extends between the outer surface and channel for receiving side branches of the vessel. The slot contains a blade for cutting the side branches and electrocauterizing plates for sealing the cut ends of the side branches. An opening may be provided for application of a ligation device to the side branch. The apparatus may be inserted into an incision in a patient's body and advanced along the length of a vessel to endoscopically dissect, ligate and transect the side branches to harvest the main trunk of the vessel to support subsequent surgical procedures.

17 Claims, 9 Drawing Sheets

APPARATUS FOR ENDOSCOPIC HARVESTING OF ELONGATE TISSUE STRUCTURES

RELATED APPLICATION

The present application is a continuation-in-part of co-pending application Ser. No. 08/991,976, filed on Dec. 17, 1997, which is hereby incorporated in its entirety by reference.

FIELD OF THE INVENTION

The invention relates to surgical apparatus and related methods for harvesting of elongate tissue structures. In particular, the invention relates to endoscopic harvesting of a blood vessel such as a saphenous vein to support coronary artery bypass grafting or the like.

BACKGROUND OF THE INVENTION

Blood vessels are commonly removed from the body for use in support of coronary artery bypass grafting ("CABG") procedures or the like. In addition, there is a need to take down side branches of vessels to perform an in situ bypass to avoid a fistula. For this purpose, multiple harvesting apparatus and means are known and are commonly used and practiced in the surgical field.

The saphenous vein has been the preferred vessel to be harvested for CABG procedures, although other vessels may be used to support CABG or other grafting procedures. Historically, the saphenous vein has been harvested by making a full length incision along the leg for the length of vein to be removed, accompanied by manual dissection of the vein along its length, transection and ligation of any lateral and deep tissue side branches, followed by transection and ligation of the main trunk of the vein itself and removal of a vein segment for preparation and use in the CABG procedure. Obviously, this type of procedure is quite traumatic and presents a high potential for morbidity and sepsis. Also, the procedure is time-consuming and labor intensive, and consequently is expensive.

To overcome these problems in the prior art, generally minimally invasive or endoscopic vessel removal and harvesting apparatus and means have been developed and are known in the surgical field. One such apparatus and method is disclosed in U.S. Pat. No. 5,373,840, which pertains to a method for harvesting vessels such as a saphenous vein. This procedure utilizes an endoscope having a lumen which permits the surgeon to grasp the saphenous vein by use of a grasping instrument for dissection. The endoscope may be maneuvered along the length of the vein while side branches of the vein are ligated and transected wherever encountered. This method provides for a minimally invasive technique; however, this apparatus and practice of the method provide limited visibility of the saphenous vein and its side branches because viewing is limited to the immediate area directly in front of the endoscope. In addition, illumination within the subcutaneous space created by this type of endoscope is restricted by the light emitted directly at the distal portion of the endoscope. Also, the side branches of the saphenous vein limit the maneuverability of the endoscope since the outer edge of the endoscope body is prevented from advancing along the trunk of the saphenous vein until each sequential side branch is ligated and transected. Once freed, the endoscope is then maneuvered until the next side branch is encountered. It has been found that this type of endoscope, i.e., an endoscope having a lumen, provides a working space which is very restricted because the side walls of the scope body confine the working instrumentation to a limited area.

Furthermore, use of the vessel harvesting apparatus and method described above is typically a "three-handed" approach which, in practice, may require more than one individual. One hand is required to hold and maintain the endoscope, a second hand to hold the free end of the transected vessel, and a third hand to dissect connective tissue from the vessel.

U.S. Pat. No. 4,793,346 shows a process and apparatus for harvesting a vein. Incisions are made at locations at the ends of the vein to be removed. The primary vein is then severed, and a flexible plastic guide is inserted into the vein and manually advanced inside the vein until it is exposed at the distal incision. The surgeon then advances a tube over the exterior of the primary vein, which already contains the interior vein guide. While doing so the surgeon turns and rotates the tube, which supports heated knife blades for severing and electrocauterizing side branches. However, the use of the interior vein guide raises a risk of damaging the endothelium of the blood vessel. In addition, there are no guides to protect the main trunk of the vein from the electrocautery action of the heated knives, or from the knife edges themselves.

Another apparatus and method for endoscopic vessel harvesting is shown in U.S. Pat. No. 5,667,480. This patent shows serial use of an optical dissector followed by an optical retractor for manual dissection, ligation and transection of the side branches and vessels using other equipment.

Other endoscopic apparatus and methods for harvesting of blood vessels are known in the art; however, these other methods and apparatus have not overcome numerous problems, such as possible damage of the main trunk vein during harvesting and the need to manipulate multiple tools or perform multiple time consuming, labor-intensive steps for dissection, retraction and ligation during the harvesting process.

In accordance with the foregoing, one object of the present invention is to provide an apparatus and method for endoscopic harvesting of blood vessels while protecting the main trunk of the vessel from damage so that it may be used successfully to support CABG or other surgical procedures.

Another object of the present invention is to provide an apparatus and method for endoscopic harvesting of blood vessels which minimizes the trauma to the patient associated with surgical incisions.

Yet another object of the present invention is to provide an apparatus and related method for endoscopic harvesting of blood vessels which minimize the labor and time required for harvesting.

Another object of the invention is to relieve deficiencies of prior apparatus and methods that require active dissection and control of side branches during harvesting.

A further object of the present invention is to provide an apparatus and method for endoscopic harvesting of a blood vessel whereby the functions of blunt tissue dissection, transection of side branches and cauterization or ligation of side branches may be performed with a single instrument.

A still further object of the present invention is to provide a method and apparatus for endoscopic harvesting of blood vessels whereby a single instrument may dissect a main trunk line for removal in a single pass over the length of the vessel, thus minimizing the time required for harvesting and the chance for damaging the vessel.

SUMMARY OF THE INVENTION

An apparatus and method for endoscopically harvesting a blood vessel from a patient's body are provided. The apparatus has a harvesting head, which may be made of molded plastic, that defines a channel for receiving a blood vessel and an outer surface for blunt dissection and retraction of connective tissue surrounding a vessel within the channel. The head may be mounted on an extended handle and may have a substantially ovate shape with its major axis coincident with the axis of the channel. At least one slot extends between the outer surface and the channel for receiving side branches extending from a vessel within said channel. The harvesting apparatus may include a plurality of said side branch receiving slots. Tapered dissecting and retracting surfaces may be defined by first and second longitudinal end portions of the head. At least one radial slot for receiving a side branch may extend from both tapered dissecting and retracting surfaces.

The harvesting apparatus further comprises means for severing a side branch received in the at least one lateral slot. The severing means may be a blade with one edge, for unidirectional cutting, or with two edges for bidirectional cutting. The blade may be mounted in a central portion of the head.

The at least one slot may contain means for cauterizing a side branch received in the slot, which may be bipolar electrocauterizing plates positioned on opposite sides of the slot or monopolar electrocauterizing strips. The electrocauterizing contacts may be mounted in the head at a location sufficiently removed from the channel to avoid damaging a blood vessel received in the channel.

The head may include at least one opening extending from an external surface of the harvesting head to a slot, for receiving auxiliary ligation devices.

A plurality of radial side branch receiving slots may be defined by the head. The head may have three side branch slots, each being radially oriented at approximately 90° relative to a slot adjacent to it.

A method is provided for endoscopically harvesting a blood vessel from a patient's body using the apparatus. The head of the apparatus may be inserted into an incision in a patient's body so as to position the channel of the head around a blood vessel. The head may be advanced manually along the length of the blood vessel to dissect and retract connective tissue surrounding the vessel and to cause side branches from the vessel within the channel to enter the at least one slot extending between the outer surface and channel of the head so as to transect and cauterize the side branches. The freed trunk portion of the vessel is then removed from the patient's body for use in a subsequent surgical procedure or for other applications.

BRIEF DESCRIPTION OF THE DRAWINGS

The foregoing and other objects, advantages and features of the invention, and manners in which the same are accomplished, will become apparent from the following detailed description of the invention taken in conjunction with the accompanying drawings which illustrate preferred and exemplary embodiments, wherein.

DESCRIPTION OF PREFERRED EMBODIMENTS

The present invention now will be described more fully hereinafter with reference to the accompanying drawings, in which preferred embodiments of the invention are shown. The invention may, however, be embodied in many different forms and should not be construed as limited to the embodiments set forth herein; rather, these embodiments are provided so that this disclosure will be thorough and complete, and so as to fully convey the scope of the invention to those skilled in the art. Like numbers refer to like elements throughout.

Figures 1, 2:
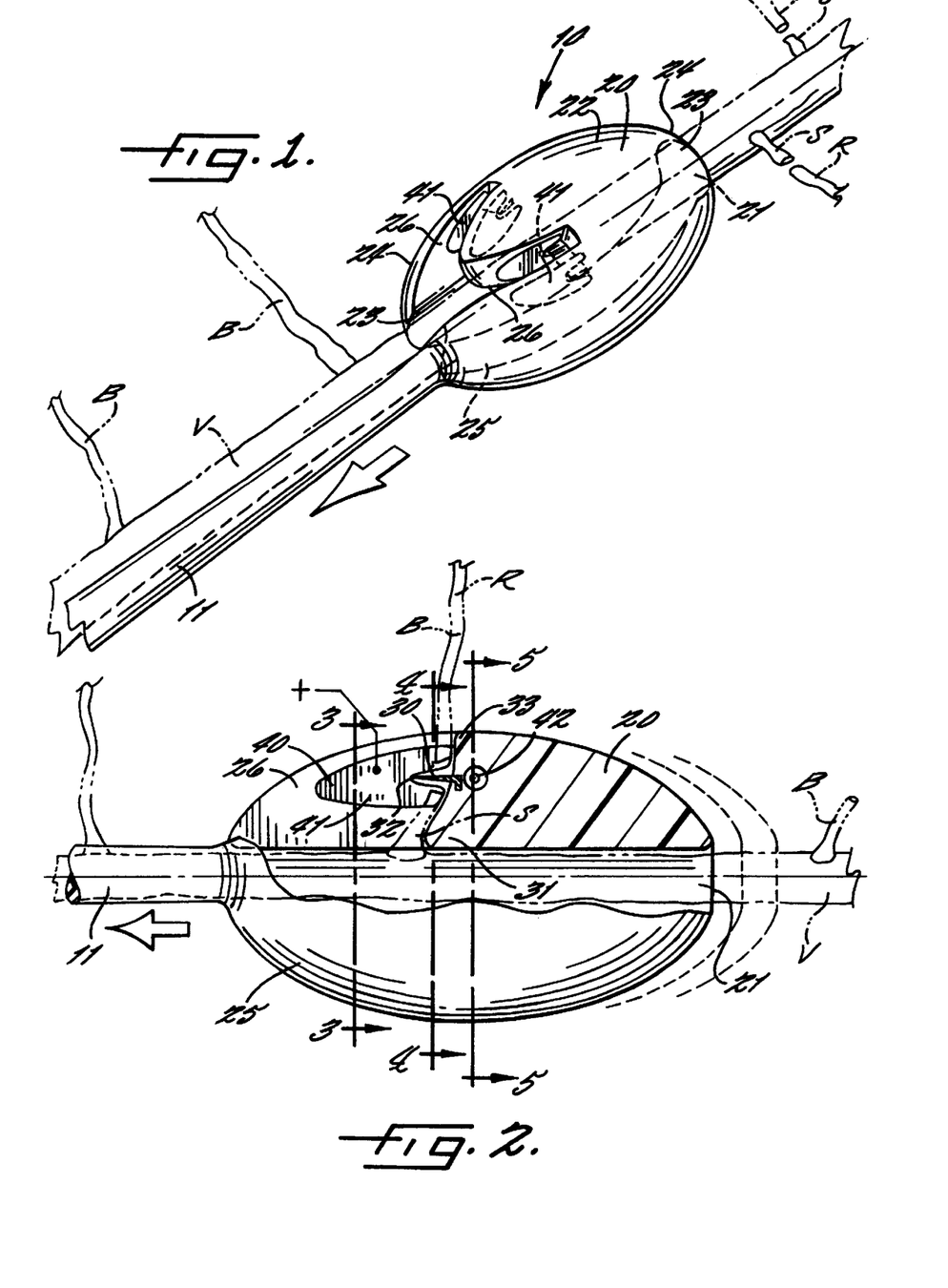
FIG. 1 is a perspective environmental view of one embodiment of a vessel harvesting apparatus made in accordance with the principles of the present invention, shown in engagement about a vessel to be harvested.
FIG. 2 is a side elevation view of the vessel harvesting apparatus illustrated in FIG. 1.

Referring now to the drawings, FIG. 1 is a perspective view of one embodiment of a new vessel harvesting apparatus made in accordance with the present invention, the harvesting apparatus being designated generally at 10, which is shown in an environmental setting with a vessel to illustrate a method of use of the apparatus. Alternative embodiments of the harvesting apparatus 10 are most clearly illustrated in FIGS. 7 and 8 so as to illustrate the structure and use of the apparatus 10.

Referring again to FIG. 1, the harvesting apparatus 10 includes an extended handle 11 from which a harvesting head 20 depends. The handle 11 may be integral with the head 20 but may be positioned at an eccentric location as illustrated in FIG. 1. The harvesting head 20 may be fixedly mounted to the handle 11 or, as an alternative, may be removably mounted by any convenient means to the handle 11. A friction fit, bayonet mount or threaded connection may be particularly suitable for interconnecting the handle 11 and head 20. The harvesting head 20 may be mounted on the extended handle 11 such that the apparatus 10 may be manually manipulated by a user such as a surgeon or other user for endoscopic harvesting of a vessel V.

The harvesting head 20 may be made of any suitable biocombatible material. It is preferred that the head 20 be made of a nonconducting material such as plastic so as to facilitate the use of electrocautery means which may be integrated within the head 20. It is particularly convenient for the head 20 to be molded of a suitable thermoplastic material, ideally as a unitary construction. The head 20 or portions thereof may be transparent or may have other suitable optical transmission characteristics adapted for use in connection with a visual endoscope during a surgical procedure. The head 20 may be used in conjunction with a visual endoscope, which may be integrally formed or provided for within the handle 11 and head 20. Alternatively, a suitable receptacle may be formed within the head 20 for receipt of conventional endoscope means for providing visual guidance of the head 20.

Figures 8, 9:
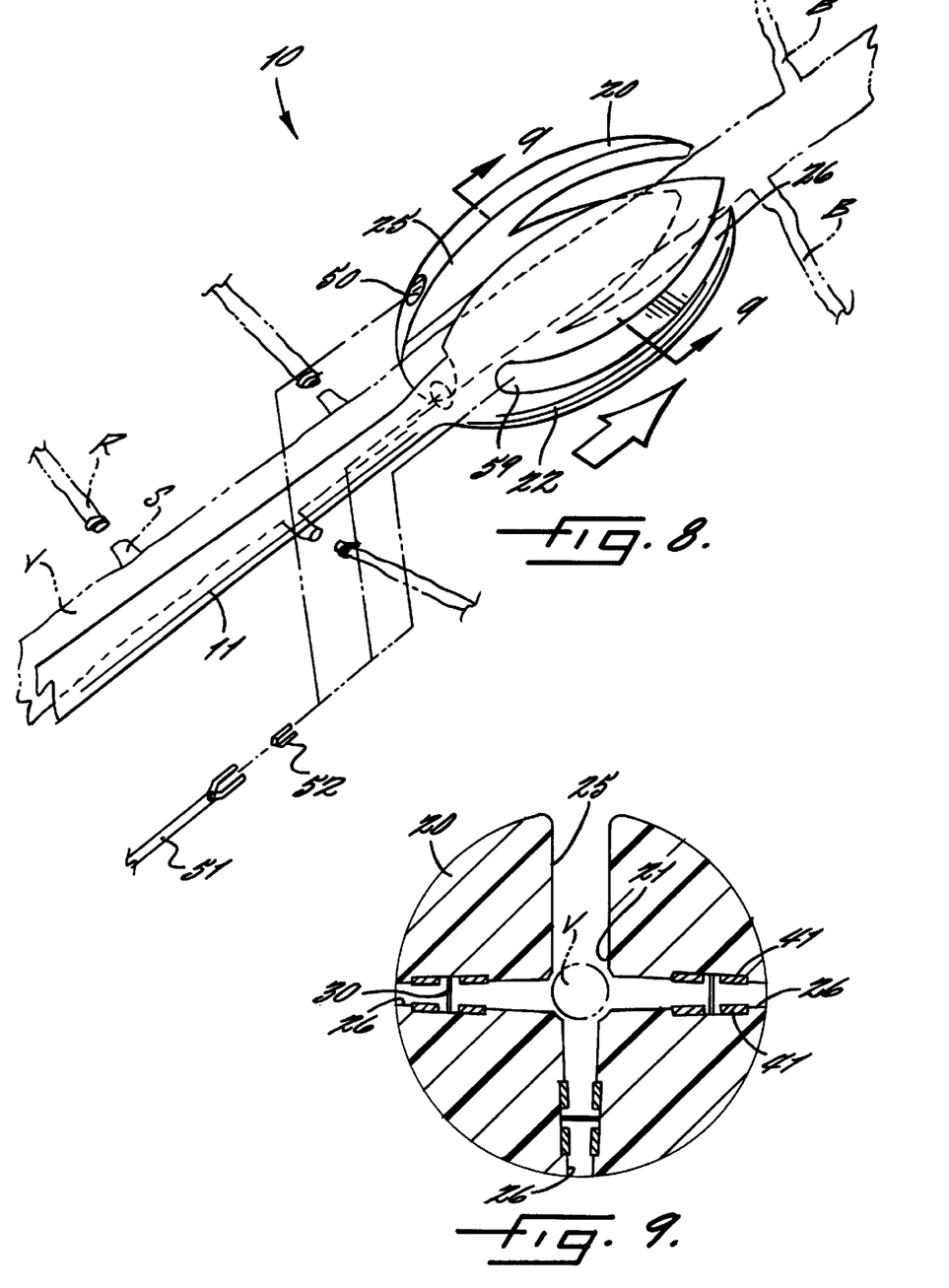
FIG. 8 is a perspective environmental view of yet another embodiment of a vessel harvesting apparatus made in accordance with the principles of the present invention, which illustrates a vessel being harvested and the use of auxiliary ligation means.
FIG. 9 is a cross-section view of the embodiment illustrated in FIG. 8, taken along line 9—9 thereof.

FIGS. 1 and 8 illustrate the harvesting head 20 in engagement around at portion of a blood vessel V to be harvested. The blood vessel V may be any appropriate vessel that one may desire to harvest; however, saphenous veins of the leg are most commonly harvested to support coronary artery bypass grafting procedures.

As shown most clearly in FIG. 8, an elongate tissue structure to be harvested by the apparatus and related method, such as a nerve or in particular, a blood vessel V such as the saphenous vein, generally has a number of side branches B extending therefrom. These branches must be cauterized or ligated, and transected, in order to harvest the trunk portion of the vessel V. A vessel such as a saphenous vein generally includes a number of side branches B extending laterally, substantially parallel to the skin, as well as a number of deep tissue side branches B which extend in a generally transverse direction relative to the skin overlying of the vessel V.

The harvesting head 20 may define a channel 21 for receiving the trunk portion of the blood vessel V. The channel 21 may run substantially throughout the entire length of the head 20. In preferred embodiments channel 21 is oriented in a direction substantially parallel to the longitudinal axis of the handle 11.

The head 20 also defines an outer surface 22. The outer surface 22 is shaped to facilitate blunt dissection and retraction of connective tissue surrounding the vessel V, particularly when the vessel V is retained within the channel 21. The outer surface 22 may also be configured for accomplishing blunt dissection when the head 20 is not engaged around the vessel V.

The outer surface 22 defined by the head 20 may take any of a variety of suitable shapes for accomplishing the dissection and retraction functions explained previously. However, it is desirable that the outer surface 22 be smoothly tapered from a point adjacent the opening 23 at one end of the channel 21 towards the widest portion of the head 20. The tapered blunt dissecting and retracting surface 24 should preferably be defined at least adjacent the opening 23 at the end of the head 20 that is to be advanced along the vessel V for harvesting. However, tapered blunt dissecting and retracting surfaces 24 may be formed adjacent each opening 23 of the channel 21 at opposite ends of the head 20.

The head 20 may have a substantially ovate shape, as illustrated in FIGS. 1, 2, 6, 7 and 8. Ideally, the major axis of the ovate shaped head should extend parallel to and coincident with the central axis of the channel 21. The widest diameter of the head 20 may be located at a medial portion of head 20, as illustrated in the side elevation views 2 and 7.

The tapered blunt dissecting and retracting surfaces 24 may be oriented on the head 20 for advancement along the vessel V when a surgeon pushes the handle 11. In this instance, the tapered surface 24 is defined at the side of the head 20 opposite the points of attachment of the handle 11. A push type harvesting head is illustrated in FIG. 8. Alternatively, the tapered blunt dissecting and retracting surface 24 may be formed at the same end as the point of the attachment of the handle 11 to the head 20, as illustrated in FIG. 1, so that the surface 24 advances along the vessel V for dissection and retraction when the surgeon pulls the handle 11. Alternately, as shown in side illustration in FIG. 7, the tapered surfaces 24 may be formed at both ends of the head 20 such that the head 20 may be advanced either by pushing or pulling of the handle 11.

Referring to FIGS. 2–5 and 9, the head 20 defines a radial groove 25 extending from the surface of the head 20 to the channel 21 along the full length of the channel 21 so as to permit the harvesting head 20 to be placed around the vessel V. The groove 25 may be oriented in any desired direction relative to the channel 21. In the embodiment shown in FIG. 1, the groove 25 extends in a direction that would face the deep tissue of the patient when in use. Alternatively, as shown in FIGS. 8 and 9, the groove 25 extends in an orientation that would essentially face the skin of the patient when the harvesting apparatus 10 is in use.

Other orientations of the access groove 25 and shapes thereof may be used to accomplish the objectives of the invention.

Radial slots, or trenches, 26 funnel the side branches B towards severing and cauterizing (and/or ligating) means therein when the apparatus 10 is advanced along the main trunk of the vessel V to be harvested. Referring again to FIG. 1, at least one trench, or slot 26 extends between the outer surface 22 of the harvesting head 20 and the channel 21 for receiving side branches B extending from the vessel V within the channel 21. Any desired plurality of slots 26 may extend in a substantially radial direction around the periphery of the head 20. In the embodiment shown in FIGS. 1–4, two side branch receiving radial slots 26 are defined by the head 20 and are oriented at about 60° relative to each other and at about 120° relative to the longitudinal groove 25. However, as illustrated in FIGS. 8 and 9, a preferred embodiment of the invention utilizes three side branch receiving slots 26. The three slots 26 in this embodiment are oriented at approximately 90° relative to the adjacent slot 26 and are further oriented in a substantially quadrilateral relationship with respect to the radial groove 25. In this embodiment, two of the radial slots 26 extend substantially laterally from the head 20 so as to engage side branches B that extend substantially parallel to the surface of the skin overlying a subcutaneous vessel V such as a saphenous vein. Another slot 26 extends in an orientation that, when used, is substantially transverse to the skin surface of the patient, for engaging side branches B that extend into the deep tissue of the patient.

A greater or lesser number of side branch B receiving slots 26 may be formed in the head 20. It is contemplated that six or more slots 26 may be formed in the head for use in suitable situations. The multiple slots 26 may extend at substantially uniform intervals around the periphery of the head 20, or in any desired orientation that may be useful for harvesting any particular vessel V.

Figure 7:
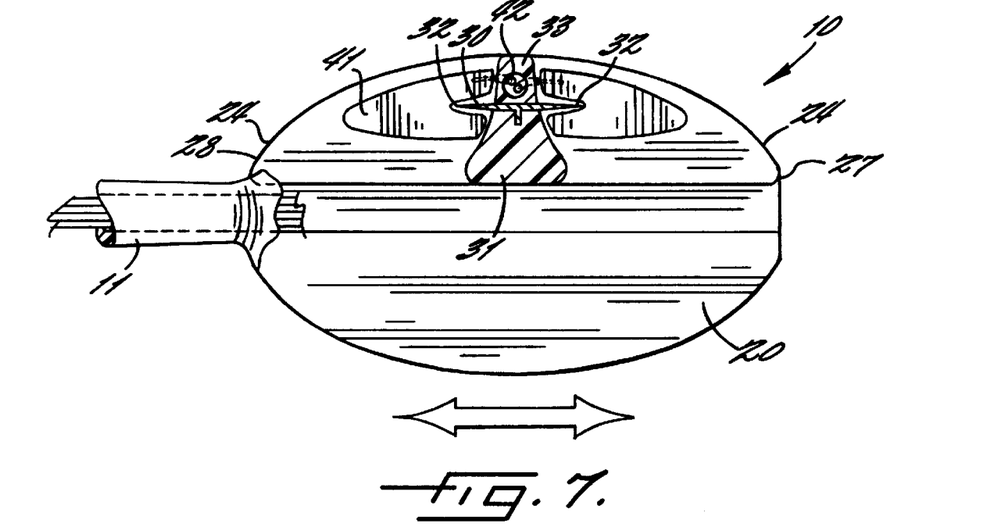
FIG. 7 is a side elevation view of another embodiment of a harvesting apparatus made in accordance with the principles of the present invention.

In heads 20 intended for advancement in a singular direction during harvesting, as illustrated in FIGS. 1 (pull direction) and 8 (push direction), the slots 26 may extend between the channel 21 and the tapered blunt dissecting and retracting surface 24 only in the direction of advancement of the head 20. Alternatively, if it is desired to enable the head 20 to be advanced bidirectionally along the vessel V, the slots 26 may extend along the full length of the head 20 and would thereby extend between fore and aft blunt dissecting and retracting surfaces 24, as shown in FIG. 7.

Referring to FIG. 2, a vessel V is shown retained within the channel 21 and a side branch B is shown within the slot 26.

The head 20 of the harvesting apparatus 10 may include means 30 for severing a side branch B received in at least one side branch receiving slot 26, as shown in FIG. 2. In preferred embodiments, the severing means 30 is a blade positioned within the head 20 at a desired distance removed from the channel 21. The blade 30 or other severing means may be retained by any suitable means within the head 20. In the embodiments illustrated herein, the blade 20 may be fixedly retained within the slot 26 by integrally molding the head 20 around the blade 30 during the manufacture of the head 20.

The space between the channel 21 and the blade 30, together with the deflector 31, protect the main trunk of the vein V from damage by the blade 30. The deflector 31 may generally underlie the blade 30 and may be rounded at its leading edge, where it adjoins the channel 21, and may be tapered so as to fall back away from the blade 30 to assist in severing the side branch B as the head 20 is advanced along the vessel V.

In a bidirectional harvesting head, as illustrated in FIG. 7, the severing means may be a blade 30 having two edges 32 oriented for bidirectional cutting of side branches B.

The blade 30 may be mounted in a central position within the harvesting head 20. Blades 30 may be positioned within each of the slots 26, or alternatively, may be positioned in selected ones of the slots 26.

The head 20 may also include means for marking the cut side branches R so as to identify them for subsequent surgical steps, such as application of clips or staples. The marking means may be a felt pad contained within a slot 26. The pad is impregnated with a dye or other suitable marker substance. Thus, when a side branch B slides through the slot 26, the pad contacts and applies a dye to a desired portion of the branch B so that the portions R can be identified visually or by other detection means.

The harvesting head 20 may also include means 40 for cauterizing a side branch B received in at least one of the side branch receiving slots 26. As illustrated in FIGS. 1 and 2, the means 40 may consist of bipolar cauterizing plates 41 positioned on each side of the slots 26. The bipolar plates 41 may be charged by an electric current via leads 42 that extend down the length of the handle 11, as illustrated in FIGS. 2–6, and in to the head 20. The leads 42 may extend such that the plates 41 are arranged in an electrical series with each other, in parallel, or in any other suitable electrical arrangement. If the handle 11 and head 20 are removable from each other, suitable electrical connection means may be provided between the two. As shown in FIGS. 2 and 5, the leads 42 may extend in a substantially peripheral orientation behind the blade 30 and the plates 41 within the body of the head 20, behind the deflector 31.

The application of electrical current to the cauterizing means 40 may be controlled manually by the operator of the apparatus 10 via a switch or other suitable means. The switch means may be located on the handle 11 or at some remote location (i e., a foot switch). Alternatively, the cauterizing means 40 may be automatically energized continuously, or may be energized at selected times when a side branch B enters a slot 26.

The voltage and current supplied to the cauterizing means 40 is sufficient to cauterize at least the remaining portion R of a side branch B that is severed, as shown in FIG. 2. Alternatively, the orientation of the means 40 and the supply of current and voltage thereto may be sufficient to cauterize both the remaining portion R of the side branch B as well as the severed portion S of the side branch B. The orientation and location of the cauterizing means and the levels of voltage and current supplied thereto are such that the main trunk portion of the vessel V is not damaged during the harvesting process, as will be apparent to persons of skill in the art.

Figure 3:
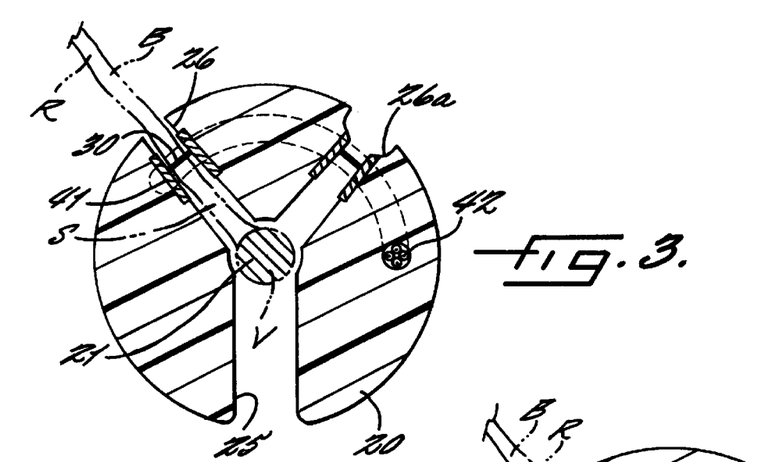
FIG. 3 is a cross-section view of the embodiment shown in FIG. 2, taken along line 3—3 thereof.
Figures 4, 5:
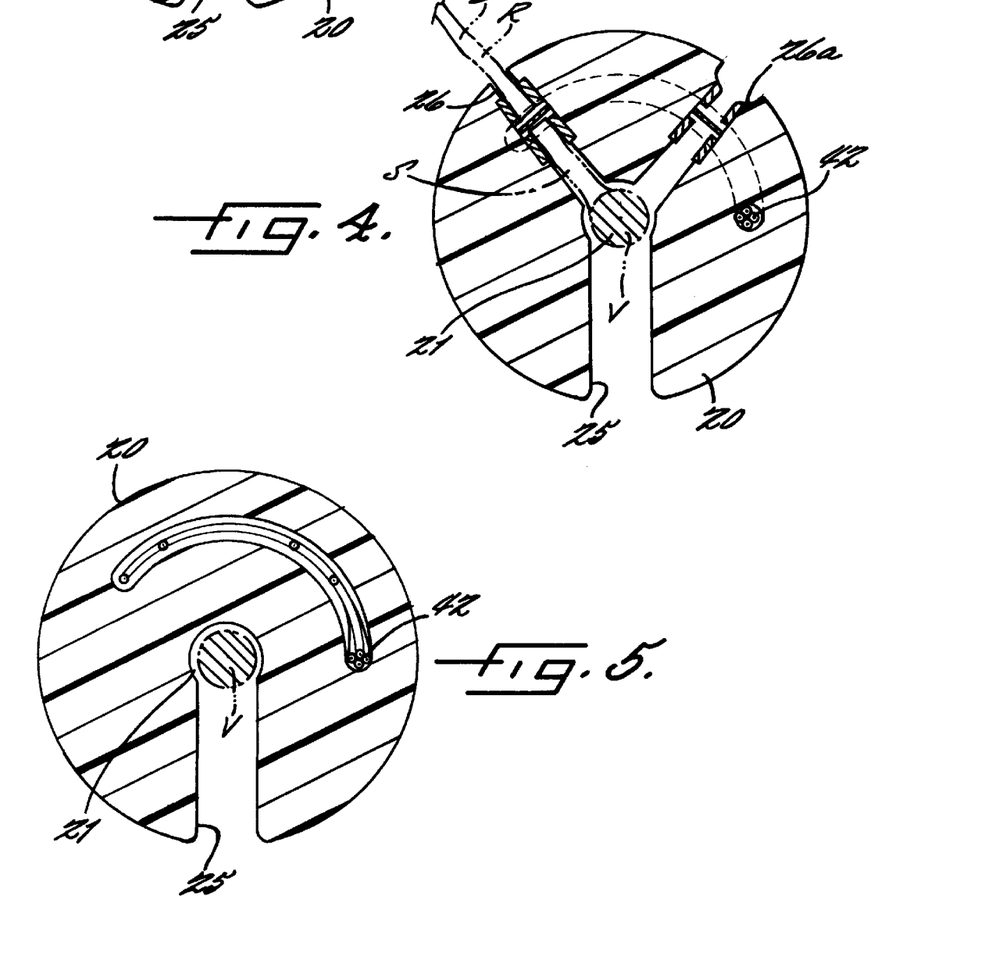
FIG. 4 is a cross-section view of the embodiment shown in FIG. 2, taken along line 4—4 thereof.
FIG. 5 is a cross-section view of the embodiment shown in FIG. 2, taken along line 5—5 thereof.
Figure 6:
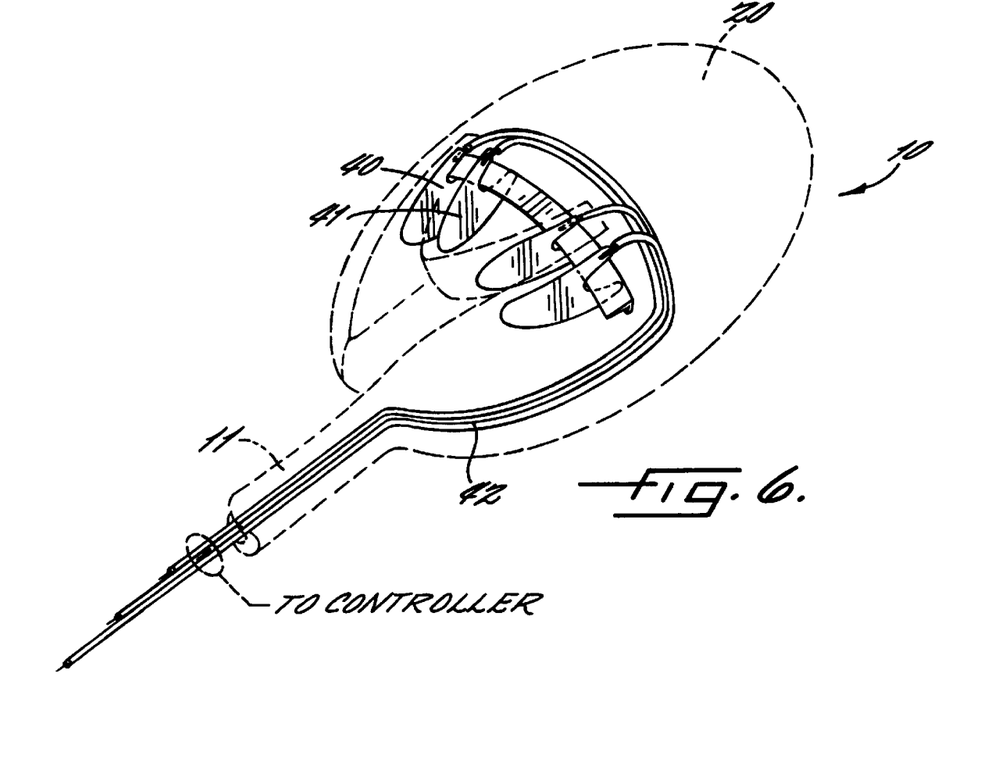
FIG. 6 is a partially schematic perspective view of a vessel harvesting apparatus made in accordance with the present invention which depicts one arrangement for supplying electrical power to electrocautery means within the apparatus.

Further illustration of a side branch being severed and cauterized is provided in FIGS. 3 and 4. In FIG. 3, the main branch of the vessel V being harvested is shown positioned within the channel 21. A side branch B is shown within the left-hand slot 26 in engagement close to the blade 30 and the cauterizing plate 41. In FIG. 4, the head 20 has been advanced along the length of the vessel V such that the side branch B has been severed into two separate parts: the remaining portion R and the severed portion S. At this point, at least the portion R of the branch B has been cauterized by the means 40, and the portion S of the branch B may also have been cauterized.

The cauterizing means 40 such as the plate 41 may be located relatively closer to the channel 21 or relatively closer to the surface 22 of the head 20 with respect to the blade 30. As yet another alternate, multiple cauterizing means 40 such as plates 41 may be positioned radially closer to the channel 21 as well as further removed from the channel 21 to assist in severing and cauterizing of the side branches B.

As still another alternative, monopolar electrocauterizing strips may be used as the cauterizing means 40. The strips 40 may be positioned on opposite sides of a slot 26, or alternatively, may be positioned or embedded within the deflector 31.

The deflector 31 may also include the part 33 that extends radially outwardly from the blade 30, as shown in FIGS. 2 and 7. The part 33 assists in protecting nerves from being cut or otherwise damaged by the blade 30 and the electrocauterizing means 40.

The tapered dissecting and retracting surface 24 may be defined on first and second end portions of the harvesting head, denominated on FIG. 7 as parts 27 and 28, respectively. The side branch receiving slots 26 may extend from both ends 27 and 28, and the tapered dissecting and retracting surfaces may be defined at both ends 27 and 28 of the head 20.

The handle 11 may extend in one embodiment from the tissue dissecting and retracting surface 24. Alternatively, the handle 11 may be mounted on an end of the head 20 opposite the surface 24, and in an embodiment where two such surfaces 24 are defined at ends 27 and 28 of the head 20, the handle 11 may extend from one such surface 24.

As shown in FIG. 8, the head 20 may include at least one opening or receptacle 50 for receiving means for ligating the side branches B, such as a stapler or other clip applying apparatus 51 that may be of a type commonly used in the art. The stapler 51 may be inserted endoscopically by the surgeon such that the opening 50 may be used to guide the end of the stapler 51 to the appropriate location adjacent the side branch for application of a staple or clip 52 in a conventional manner. The remaining portion R of the side branch B, after severing would therefore include a ligation clip on a free end thereof, as illustrated in FIG. 8. Also, clip or staple applying apparatus may be integrally formed within the head 20.

A plurality of the openings or receptacles 50 may be defined within the head 20 so as to extend therethrough in relation to one or more of the slots 26. The openings 50 and the use of the stapler and staples 51 and 52 may supplement the cauterizing means 40 or may be an alternative thereto. The openings 50 and the conventional stapler and staples 51 and 52 may be the means for a ligating side branches in lieu of the cauterizing means 40.

As a variation of the openings 50, one or more slots 59 may be provided in the head 20 for receiving a stapler or the like and guiding same to a side branch. Each slot may extend from the surface of the head 20 to a position similar to that defined by the opening 50 shown in FIG. 8. The slot may be formed in the push-type, pull-type or bidirectional head 20. The slot for receiving the stapler may be coextensive with the side branch receiving slots 26. This arrangement is particularly useful in the bidirectional and pull-type heads 20. In this embodiment, a path for guiding the stapler may be defined by a surface portion 26a of the slot 26 with a cross-sectional width greater than the width of other portions of the slot 26. This wider portion corresponds to the size of the stapler 51. Thus, the stapler will rest in the wider portion of the slot 26, without falling into the narrower portion of the slot 26, and the stapler will slide in the wider portion to a desired position so as to apply a clip to a side branch B. The wider surface portion and narrower portion of the slot 26 may be joined by a smoothly radiused curve. In addition, stop means such as a spring-loaded side ball or the like may be provided to give the user positive indication when the stapler has reached a desired location relative to a side branch B within the head 20.

A further groove or other guide means may be provided along the length of the handle 11 for guiding a stapler 51 to the head 20. The stapler 51 may be positioned in or adjacent to the slot in the handle 51 so as to assist the surgeon in guiding the stapler 51 to the head 20 while the apparatus 10 is received within the body of a patient. Thus, the groove in the handle 11 facilitates endoscopic application of staples to side branches B.

When the head 20 has been advanced along the entire length of the trunk portion of the vessel V to be harvested, the trunk vessel V may be cut and ligated via standard means such as endoscopic scissors or the like. Alternatively, the head 20 may be provided with an integral end cutting device for transecting the main trunk of the vessel V at a desired location. For this purpose, a blade or other suitable means may be provided within the head 20 and may be brought into engagement with the trunk vessel V received within the channel 21 to sever the vessel V at a desired point. The vessel V may be ligated by conventional means, or alternatively, endoscopic means for ligating the trunk vessel V may be provided within the head 20 as well. The means for ligating and/or transecting the vessel V may be brought into engagement manually by provision of control means at the operating end of the handle 11. To this end, a twist mechanism may be particularly advantageous, although a trigger actuator or other means may also be suitable.

The present invention is intended to provide for a one-step harvesting of a vessel. Alternatively, however, the apparatus 10 and the related method of using the apparatus may be employed in conjunction with prior art methods of performing anterior vein dissection as a preliminary step before harvesting. The apparatus and method provide for harvesting of vessels to support CABG procedures, as well as for taking down of side branches to perform in situ bypasses.

Use of the present invention greatly reduces, and in some cases may even eliminate, the need for external clip applying devices such as a stapler 51. In addition, the invention may decrease or eliminate the need to actively dissect and control individual side branches. Also, the apparatus protects the main trunk portion of the vessel V during dissection. The apparatus and related method provide reduced invasiveness of minimal-access saphenous vein harvesting as well as markedly decreased harvest times.

The present invention permits harvesting of substantial lengths of a vessel V to be accomplished by making only a relatively small incision at a desired location, which may be removed from points of particular concern such as the ankle or abdominal portion of the patients body. When harvesting the saphenous vein it has been found particularly advantageous to form the incision for insertion of the endoscopic apparatus 10 at a location immediately above the knee.

Also provided is a method of using the inventive apparatus described herein to harvest a vessel V, particularly for use in supporting a coronary artery bypass grafting procedure. The incision as described above is preferably made immediately above the knee of a patient after the location of the vein has been identified visually, or by palpation or by other means. The head 20 may be advanced subcutaneously adjacent the superior surface of the vessel V to perform an initial blunt dissection. However, an anterior dissection step may be performed using conventional equipment. Thereafter, the head 20 may be positioned such that the vessel V is retained within the channel 21. If a "pull" type embodiment is being used, the head 20 is then retracted by the surgeon by pulling on the handle 11. Side branches B are therefore funnelled into the slots 26 and come into engagement with the blade 30 and the cauterizing or other ligating means 30. The side branches are severed in serial fashion as the head 20 is advanced along the desired length of the vessel V.

When the incision is made immediately above the knee, the head may be advanced downwardly, i.e., toward the ankle, for harvesting a lower section of the saphenous vein. Alternatively, or in combination with the harvesting of the lower portion of the vessel, an upper portion of the saphenous vein may be harvested by inserting the head 20 into the incision above the knee and extending it toward the abdomen.

Subsidiary incisions may be made adjacent the abdomen or near the ankle, or at any other desired location, if necessary for transecting the vessel V to be harvested.

When a "pull" type head 20 is used as shown in FIG. 1, the distal end of vessel V to be harvested may not be transected until after the side branches B have been cut and cauterized or ligated. The user may hold the distal end of the vessel V in position as tensile forces are placed on the vessel V while the head 20 is traversed along its length in a pulling fashion.

When the head 20 is configured in a "push" type arrangement such as shown in FIG. 8, the end of the vessel V adjacent the primary incision must be retained in place. The vessel V may not be cut underlying the primary incision until after the side branches B have been dissected, transected and ligated. Also, the end of the vessel V underlying the primary incision may be retained in place by suitable conventional instrumentation.

Figures 10, 11:
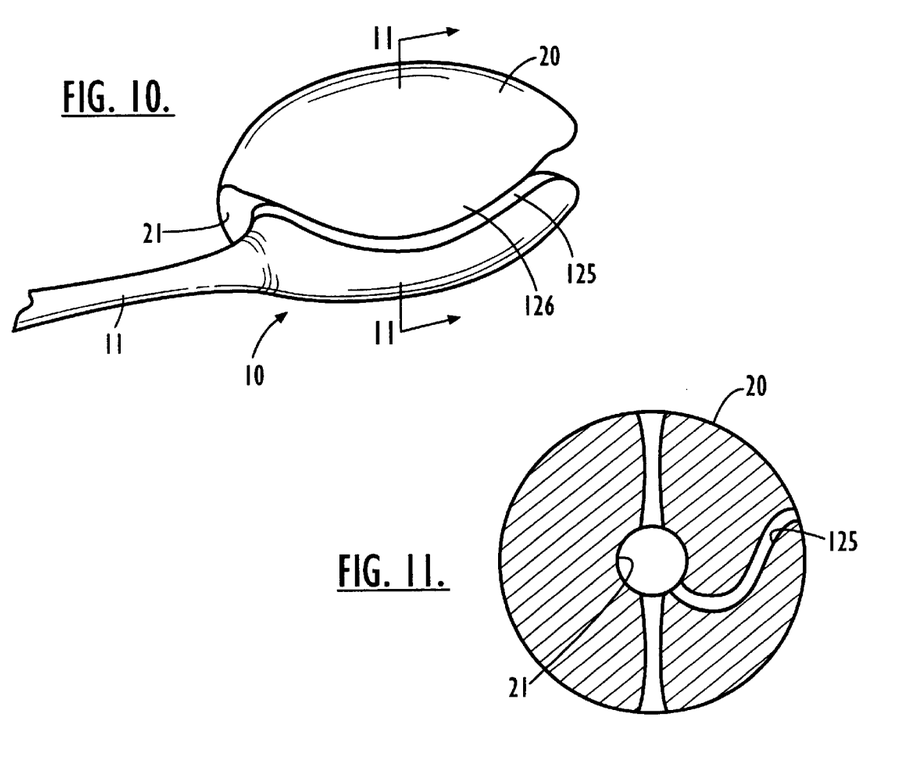
FIG. 10 is perspective view of another embodiment of a vessel harvesting apparatus made in accordance with the principles of the present invention.
FIG. 11 is a cross-section view of the embodiment shown in FIG. 10, taken along line 11—11 thereof.
Figure 13:
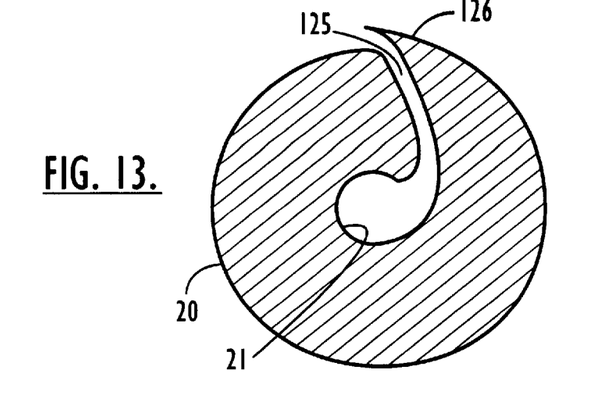
FIG. 13 is an alternative cross-section view of the embodiment shown in FIG. 10, taken along line 11—11 thereof.

Referring now to FIG. 10, an alternate embodiment of the harvesting head 20 of the apparatus 10 is shown in which the access groove 125 is provided in a manner to aid in retaining a vein V being harvested within the central channel 21. In FIG. 10, a lip 126 may be provided along the widest or other portion of the head to help guide the vein into the groove 125 and further into the central channel 21. Referring to FIG. 13, the lip 126 and groove 125 are illustrated in cross-section so as to illustrate the entry by which a vein V may be positioned within the central channel 21 of the head 20. Alternatively, referring to FIG. 11, the channel 125, may be formed in an arcuate path, or any other path other than radially linear from the central channel 21 to the exterior of the head 20. A surgeon may manipulate the apparatus 10 by twisting and/or rotating the head 20 to urge a vein V into the central longitudinal channel 21 at any point in the harvesting operation.

Alternatively, it is envisioned that the channel 21 could be closed completely to retain the vein V within the central channel 21. This could be accomplished by mechanical means that can readily be envisioned and which could be operated by twisting or other manual manipulations as well as by automatic means. The mechanical closure of the central channel 21 may be provided regardless of the shape of the groove 25 or curved grooves 125.

Another advantage of the lip 126 illustrated in FIGS. 10 and 13 is that this overhanging lip portion could be formed to function as a lateral vein dissector. As shown in FIG. 1, the lip can be gently curved, or alternatively, sharp transverse cutting surfaces could be formed so that dissection could be performed as the head is advanced along the length of a vein V.

In a preferred embodiment, the overhang of the lip 126 may cover about the central one-third portion of the length of the head 20, although it may extend over a greater or lesser portion, as desired.

Figure 12:
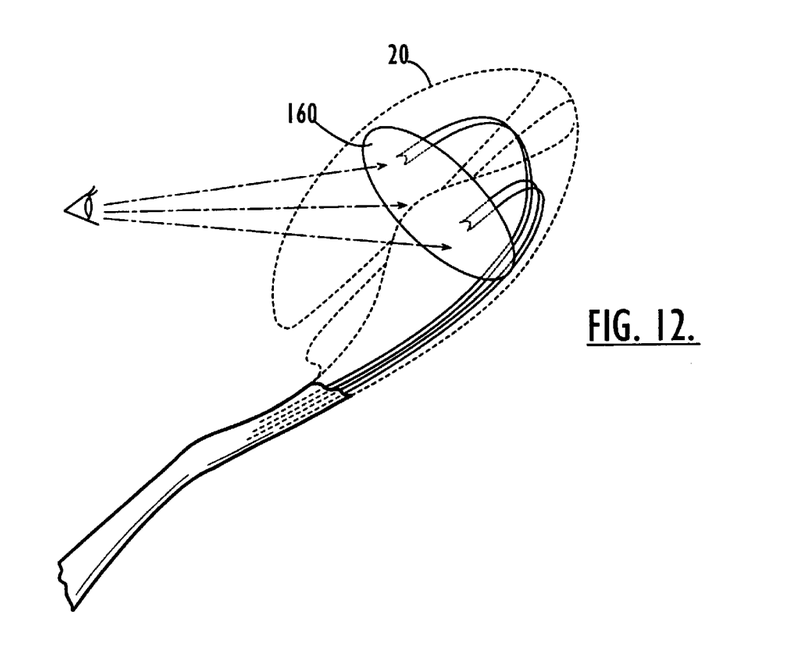
FIG. 12 is a perspective view illustrating another embodiment of a vessel harvesting apparatus made in accordance with the principles of the present invention.

Referring to the embodiment shown in FIG. 12, a clear head 20 may be provided to aid a surgeon's manipulation of the device in surgery. However, it is conceivable that structures in the head such as electrocautery devices could be distracting to the surgeon, and furthermore, it may be advantageous in practice to limit the visibility of the surgeon within the head to avoid confusion and to provide a background for seeing various structures within the patent's body. Accordingly, it may be advantageous to provide an opaque shield 160. The shield may be made of any suitable means and could comprise any portion of the head 20. The shield could be radially planar, as illustrated in FIG. 12, or it could be cone-shaped or any other desirable shape so as to provide a superior background for viewing side branches or the like. Of course, the head 20 may be formed so that the non-slotted end would be entirely opaque whereas the leading, slotted end would be transparent.

Figure 14:
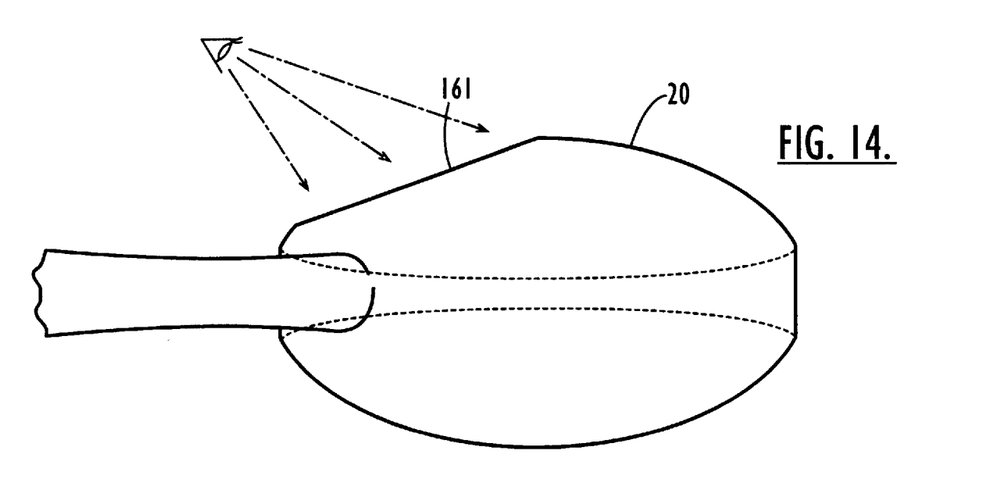
FIG. 14 is a side elevation view of another embodiment of a vessel harvesting apparatus made in accordance with the principles of the present invention.

Referring to FIG. 14, the head 20 may be provided with one or more flat surface portions constituting a viewing window 161 to facilitate clear vision of structures contained within the head 20. For example, the curved surfaces of the head 20 may cause distortion, magnification or other problems that could be eliminated by the provision of a window 161 via a flat surface. Alternatively, the viewing window 161 may be formed differently by either accentuating (i.e., making more convex), flattening or reversing the curvature (ie., making concave) to enhance visualization of vessels and/or side branches.

Figure 15:
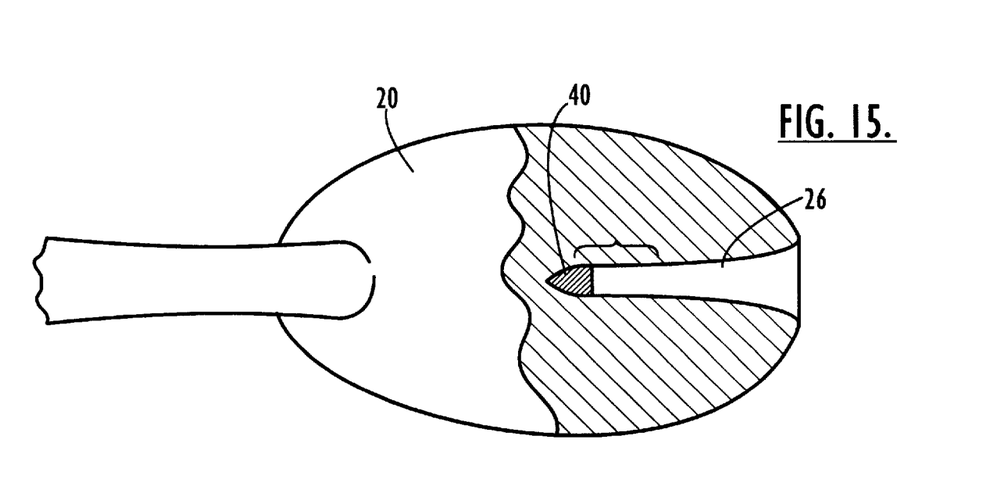
FIG. 15 is a partially sectional side elevation view of yet another embodiment of a vessel harvesting apparatus made in accordance with the principles of the present invention.

Another embodiment of the head 20 is shown in FIG. 15. In this embodiment, the slots 26 for guiding side branches B may be tapered in a longitudinal direction to increase the prominence of the leading edge of the slot and to bring the sidewalls of the slot closer together in the region of the cautery pads 40. Also, referring to FIGS. 16–20, the rear edge structure of the slots 26 may be tapered in a radial direction, such that a leading edge near the cautery pads 40 and severing blade 30 initially comes into contact with a side branch B as the head 20 is advanced along with a vein V. This structure is believed to enhance the cutting ability of the blades 30, and would also provide a measure of safety in that the cautery and severing could be applied at a greater distance removed from the main vein to be harvested. Furthermore, this structure may provide a longer remnant of the side branch B attached to the main vein V after severing and cautery.

Figure 16:
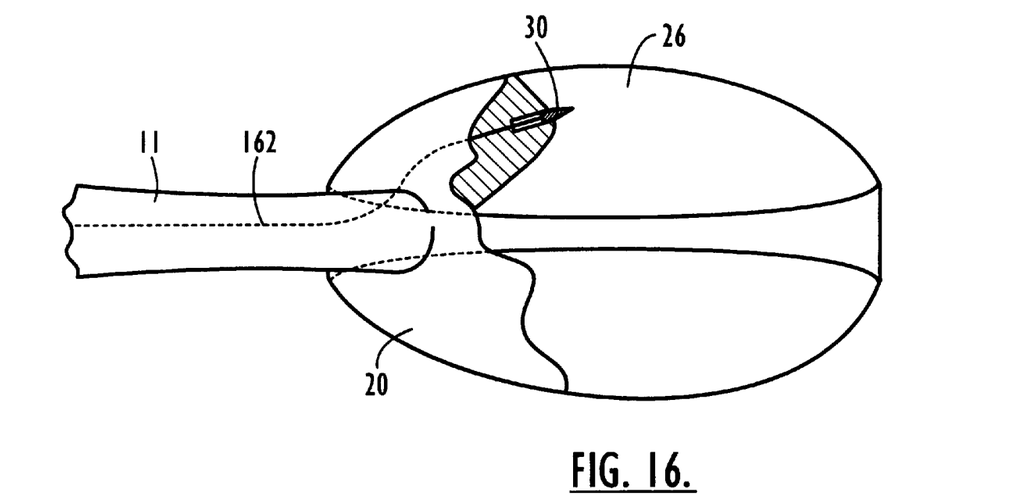
FIG. 16 is a partially sectional side elevation view of yet another embodiment of a vessel harvesting apparatus made in accordance with the principles of the present invention, which illustrates a severing blade in a first position.
Figure 17:
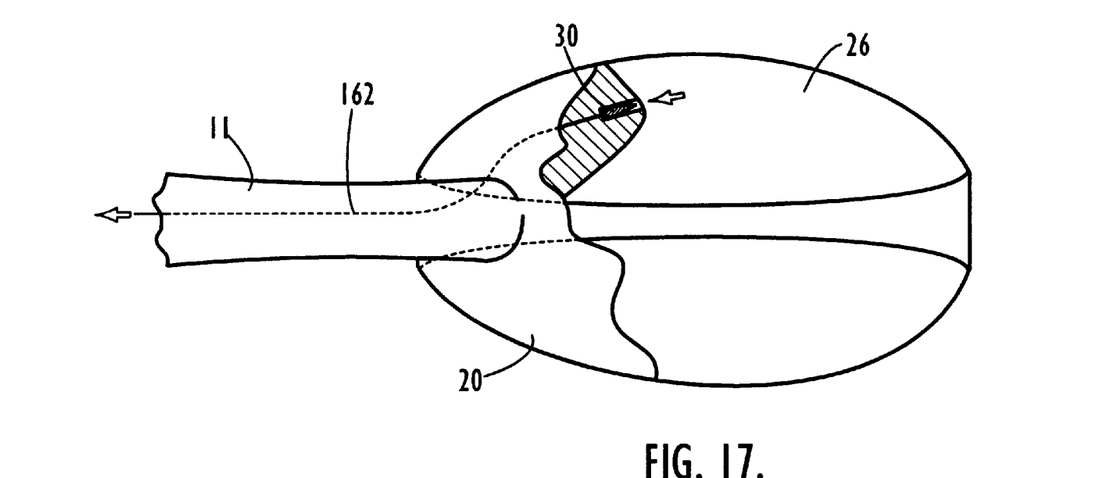
FIG. 17 is another partially sectional side elevation view of the embodiment shown in FIG. 16 but in which the severing blade is shown in a second position.

Referring to FIGS. 16 and 17, the blade 30 may be moved in a generally fore and aft direction by push-pull means 162. The blade 30 could be biased in either the exposed position shown in FIGS. 16 or in the retracted position of FIG. 17. A cable, wire or rod or the like could be used to move the blade 30 back and forth to provide enhanced cutting.

Figure 18:
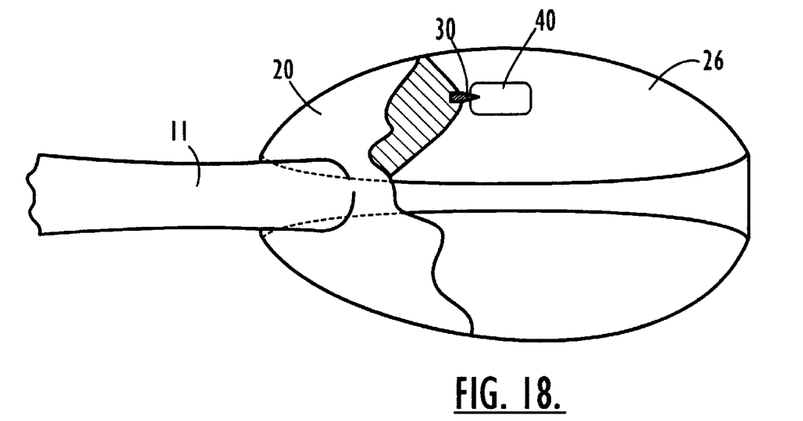
FIG. 18 is a partially sectional side elevation view of yet another embodiment of a vessel harvesting apparatus made in accordance with the principles of the present invention.
Figure 19:
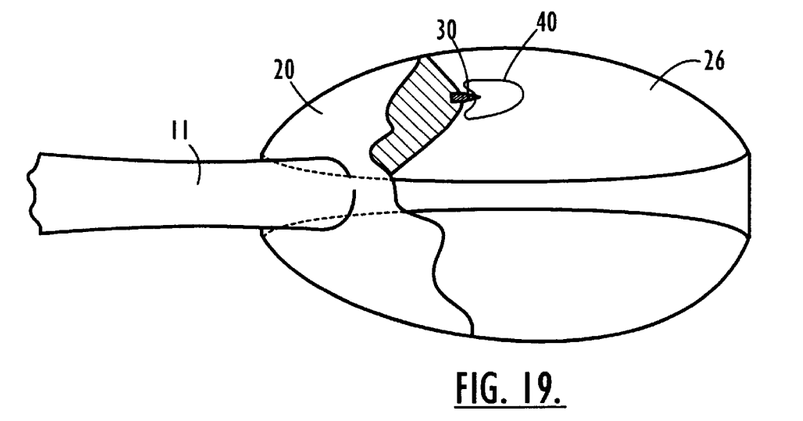
FIG. 19 is a partially sectional side elevation view of yet another embodiment of a vessel harvesting apparatus made in accordance with the principles of the present invention.
Figure 20:
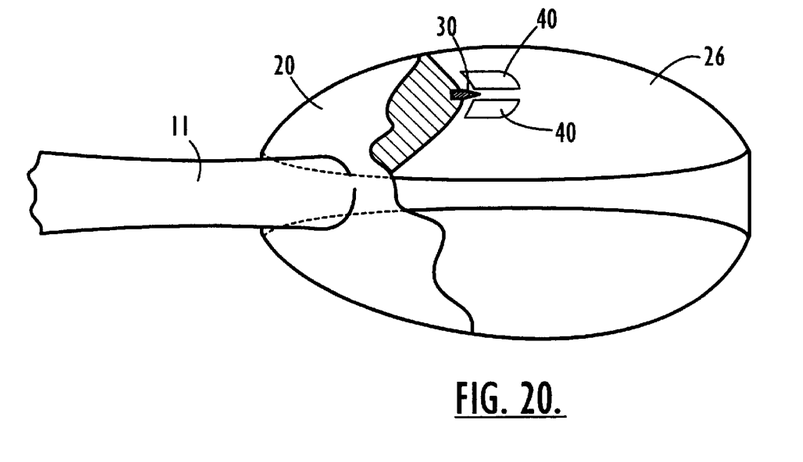
FIG. 20 is a partially sectional side elevation view of yet another embodiment of a vessel harvesting apparatus made in accordance with the principles of the present invention.

Referring to FIGS. 18 through 20, the blade 30 may be positioned in a stationary, generally longitudinally forward-facing orientation.

Also referring to FIGS. 18 through 20, the cautery pads 40 may take any various positions, some of which are illustrated herein and others of which will be apparent to persons of skill in the art. The size and location of the cautery pads may be selected to fully utilize the taper of the slot 26.

Figure 21:
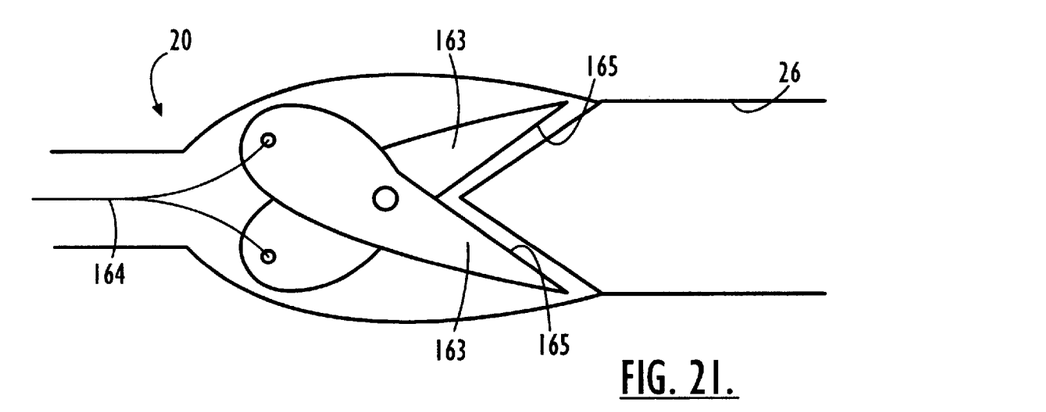
FIG. 21 is a schematic illustration of another embodiment of severing blades for use in the present invention, in which the blades are illustrated in a first position.
Figure 22:
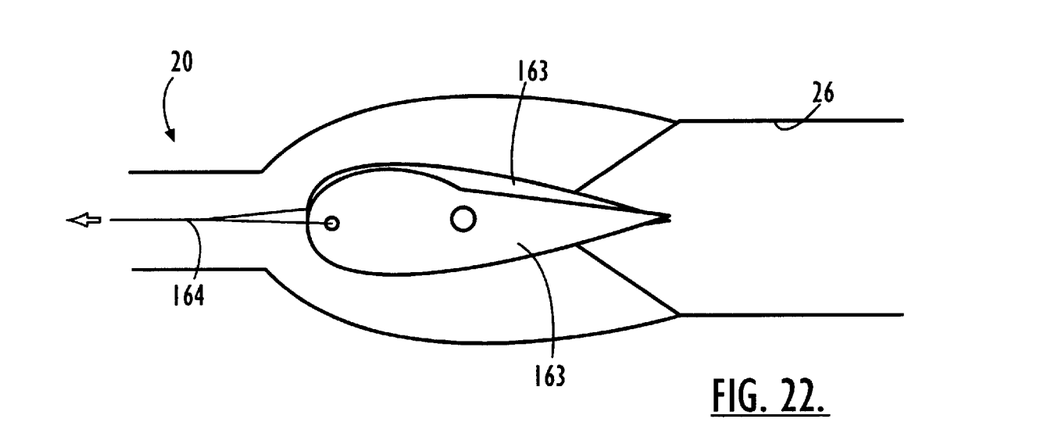
FIG. 22 is another schematic illustration of the embodiment shown in FIG. 21, but in which the severing blades are shown in a second position.

Finally, referring to FIGS. 21 and 22, a severing means 163 may be provided in the head 20 at the end of the slot 26 for severing side branches B. The blades may be activated by pulling on a wire, cable or other suitable means 164. The blades 163 may be biased in the open or closed position, as shown in FIGS. 21 and 22, respectively. Thus, in use the head 20 may be advanced until a side branch B rests in the groove 165 between the open blades 163, as shown in FIG. 21. Thereafter, the surgeon may engage the wire, cable or other activating means 164 to urge the blades 163 together so as to cut the side branch B. Alternatively, the blades 163 may be formed so that the front edges thereof form a cutting edge to sever side branches without opening or closing as the head 20 is advanced.

Many modifications and other embodiments of the invention will come to mind to one skilled in the art to which this invention pertains, having the benefit of the teachings presented in the foregoing descriptions and the associated drawings. Therefore, it is to be understood that the invention is not to be limited to the specific embodiments disclosed, and that modifications and other embodiments are intended to be included within the scope of the appended claims. Although specific terms are employed herein, they are used in a generic and descriptive sense only and not for purposes of limitation.

That which is claimed:

1. An apparatus for endoscopically harvesting an elongate tissue structure from a patient's body, comprising:
   a harvesting head defining a channel for receiving an elongate tissue structure, said head having a tapered end defining an outer surface that tapers toward said end in a longitudinal direction of said channel for blunt dissection and retraction of connective tissue surrounding a structure within said channel;
   at least one slot having an opening proximate said tapered end and extending between said outer surface and said channel, for receiving side branches extending from a tissue structure within said channel; and
   means for transecting a side branch received in said at least one slot.

2. The harvesting apparatus defined in claim 1 wherein said channel comprises a central channel extending along the length of said head for receiving an elongate tissue structure for harvesting, and further comprising a groove extending from said central channel to said outer surface of said head such that said head may be manipulated to position the elongate tissue structure within said central channel.

3. The harvesting apparatus defined in claim 2 further comprising a lip overhanging a portion of said groove at said outer surface of said harvesting head, said lip defining a step in a generally circumferential direction along said outer surface to facilitate capturing the elongate tissue structure in said groove.

4. The harvesting apparatus defined in claim 2 wherein said groove extends in a radially arcuate path from said central channel to said outer surface of said head.

5. The harvesting apparatus defined in claim 1 wherein a portion of said harvesting head is transparent and further comprising an opaque shield within said head.

6. The harvesting apparatus defined in claim 5 wherein said shield is generally planar and extends transversely to the axis of said head at a medial portion thereof.

7. The harvesting apparatus defined in claim 5 wherein said shield is conical.

8. The harvesting apparatus defined in claim 1 further comprising a vieaing-window defined in a transparent portion of said harvesting head.

9. The harvesting apparatus defined in claim 1 wherein said at least one slot narrows in the longitudinal direction from said opening thereof toward a terminus end thereof.

10. The harvesting apparatus defined in claim 1 wherein a rear edge of said at least one slot is tapered in a radial direction such that a medial portion of said rear edge, in the radial direction between said central channel and outer surface of said harvesting head, encounters a side branch before the remainder of said rear edge as said head is advanced along an elongate tissue structure.

11. The harvesting apparatus defined in claim 10 wherein said transecting means is stationary and mounted at said medial portion of said rear edge.

12. The harvesting apparatus defined in claim 10 wherein said transecting means comprises a blade that may be reciprocated in the longitudinal direction of said head.

13. The harvesting apparatus defined in claim 10 wherein said transecting means is a pair of blades positioned proximate said medial portion of said rear edge of said at least one slot, which blades may be pivoted to cut side branches.

14. The harvesting apparatus defined in claim 10 further comprising cautery means positioned on side walls of said at least one slot proximate said medial portion of said rear edge of said at least one slot.

15. The harvesting apparatus defined in claim 8 wherein said viewing window is a flat surface formed on a portion of said harvesting head.

16. The harvesting apparatus defined in claim 8 wherein said viewing window is a concave surface formed on a portion of said harvesting head.

17. The harvesting apparatus defined in claim 8 wherein said viewing window is a convex surface formed on a portion of said harvesting head.

* * * * *